US009480438B2

(12) United States Patent
Sakaguchi et al.

(10) Patent No.: US 9,480,438 B2
(45) Date of Patent: Nov. 1, 2016

(54) X-RAY IMAGING APPARATUS, MEDICAL IMAGE PROCESSING APPARATUS, X-RAY IMAGING METHOD AND MEDICAL IMAGE PROCESSING METHOD

(71) Applicant: Toshiba Medical Systems Corporation, Otawara-shi (JP)

(72) Inventors: Takuya Sakaguchi, Utsunomiya (JP); Hisato Takemoto, Amherst, MA (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/220,759

(22) Filed: Mar. 20, 2014

(65) Prior Publication Data
US 2014/0205061 A1    Jul. 24, 2014

Related U.S. Application Data

(63) Continuation of application No. PCT/JP2013/060713, filed on Apr. 9, 2013.

(30) Foreign Application Priority Data

May 9, 2012   (JP) ................. 2012-107940

(51) Int. Cl.
*A61B 6/02* (2006.01)
*A61B 6/00* (2006.01)

(52) U.S. Cl.
CPC ............. *A61B 6/022* (2013.01); *A61B 6/466* (2013.01); *A61B 6/486* (2013.01); *A61B 6/5205* (2013.01); *A61B 6/5264* (2013.01); *A61B 6/54* (2013.01)

(58) Field of Classification Search
CPC .... A61B 6/022; A61B 6/486; A61B 6/5205; A61B 6/5264; A61B 6/54
See application file for complete search history.

(56) References Cited

U.S. PATENT DOCUMENTS 5,034,987 A * 7/1991 Fujimoto ............... A61B 6/463
                                                        382/131
5,090,038 A * 2/1992 Asahina ................ A61B 6/022
                                                        348/E13.001

(Continued)

FOREIGN PATENT DOCUMENTS

JP      4-166135 A    6/1992
JP      7-240944 A    9/1995

(Continued)

OTHER PUBLICATIONS

International Preliminary Report on Patentability and Written Opinion issued Nov. 20, 2014 in PCT/JP2013/060713 filed on Apr. 9, 2013.

(Continued)

*Primary Examiner* — David J Makiya
*Assistant Examiner* — John Corbett
(74) *Attorney, Agent, or Firm* — Oblon, McClelland, Maier & Neustadt, L.L.P.

(57) ABSTRACT

According to one embodiment, an X-ray imaging apparatus includes an X-ray image acquisition part, a control system and a display processing part. The X-ray image acquisition part is configured to acquire X-ray image data of an object using at least one imaging system. The control system is configured to control the imaging system to acquire frames of X-ray image data corresponding to mutually different directions by moving the imaging system. At least one of the frames of the X-ray image data are acquired during a movement of the imaging system. The display processing part is configured to generate stereoscopically visible image data based on the frames of the X-ray image data.

15 Claims, 13 Drawing Sheets

(56) References Cited

U.S. PATENT DOCUMENTS

| | | | | |
|---|---|---|---|---|
| 5,448,610 A | * | 9/1995 | Yamamoto | A61B 6/022 348/E13.005 |
| 6,317,481 B1 | * | 11/2001 | Berestov | A61B 6/022 348/E13.008 |
| 2003/0215055 A1 | * | 11/2003 | Ozawa | G01N 23/04 378/62 |
| 2014/0198897 A1 | * | 7/2014 | Sakaguchi | A61B 6/022 378/37 |

FOREIGN PATENT DOCUMENTS

| | | |
|---|---|---|
| JP | 2006-136741 A | 6/2006 |
| JP | 2009-17322 A | 1/2009 |
| JP | 2011-200408 A | 10/2011 |

OTHER PUBLICATIONS

International Search Report issued on Jul. 16, 2013 for PCT/JP2013/060713 filed on Apr. 9, 2013 with English Translation.

International Written Opinion mailed on Jul. 16, 2013 for PCT/JP2013/060713 filed on Apr. 9, 2013.

Combined Chinese Office Action and Search Report issued Feb. 12, 2015 in Patent Application No. 201380001164.X (with English translation of categories of cited documents).

Combined Chinese Office Action and Search Report issued Jun. 3, 2016 in Patent Application No. 201380001164.X (with English translation of Categories of Cited Documents).

* cited by examiner

X-RAY IMAGING APPARATUS, MEDICAL IMAGE PROCESSING APPARATUS, X-RAY IMAGING METHOD AND MEDICAL IMAGE PROCESSING METHOD

CROSS REFERENCES TO RELATED APPLICATIONS

This is a continuation of Application PCT/JP2013/60713, filed Apr. 9, 2013.

This application is based upon and claims the benefit of priority from Japanese Patent Application No. 2012-107940, filed May 9, 2012; the entire contents of which are incorporated herein by reference.

FIELD

Embodiments described herein relate generally to an X-ray imaging apparatus, a medical image processing apparatus, an X-ray imaging method and a medical image processing method.

BACKGROUND

Conventionally, a technology for displaying X-ray diagnostic images which allow stereoscopically viewing an imaging target, such as a blood vessel, using an X-ray imaging apparatus has been proposed. Assuming that images which allow stereoscopic viewing of an imaging target are referred to as 3D (three dimensional) images, it is necessary to make an image for left eye and an image for right eye visible individually by the left eye and the right eye respectively in order to display one frame of 3D image.

Examples of method of respectively acquiring images for left eye and right eye using an X-ray imaging apparatus include a method of respectively acquiring 2D (two dimensional) X-ray projection images for left eye and right eye actually besides a method by three dimensional image reconstruction processing. The X-ray projection images for left eye and right eye can be also acquired by an X-ray imaging apparatus having a single X-ray imaging system as well as an X-ray imaging apparatus having plural X-ray imaging systems.

In case of using an X-ray imaging apparatus having a single X-ray imaging system, the X-ray imaging system is positioned to the first position by moving the C-shaped arm of the X-ray imaging apparatus. Then, an X-ray projection image for left eye corresponding to the first position can be acquired with stopping the X-ray imaging system. Next, the C-shaped arm of the X-ray imaging apparatus are moved to position the X-ray imaging system to the second position. Then, an X-ray projection image for right eye corresponding to the second position can be acquired with stopping the X-ray imaging system. Alternatively, the X-ray projection images for left eye may be acquired after acquiring the X-ray projection images for right eye.

On the other hand, X-ray projection images for left eye and right eye can be acquired using an X-ray imaging apparatus having two X-ray imaging systems. In this case, the X-ray projection images for left eye and right eye can be acquired at a same timing by positioning the two X-ray imaging systems appropriately.

The X-ray projection images for left eye and right eye acquired as described above can be used as two-parallax images for displaying a 3D image. As a method of displaying one set of two-parallax images as a 3D image allowing stereoscopic viewing, a method of displaying images for left eye and right eye alternately with a time division so as to be viewed through a dedicated glasses, a method of displaying images for left eye and right eye on a dedicated display without using a glasses, and the like are known.

Especially, acquiring X-ray projection images for left eye and right eye at a same timing using an X-ray imaging apparatus having two X-ray imaging systems makes it possible to display a 3D image, having an improved image quality, less influenced by a motion of an object.

Furthermore, generating two-parallax images by three dimensional image reconstruction processing makes it possible to display 3D images allowing stereoscopic viewing from various observation directions.

PRIOR TECHNICAL LITERATURE

[Patent literature 1] JPA H04-166135

However, there is a problem that the X-ray imaging apparatus having plural X-ray imaging systems has a complex structure and is expensive. Moreover, when a 3D image for stereoscopic viewing is generated by three dimensional image reconstruction processing, there is a problem that a data processing amount becomes huge and a data processing time also becomes long.

Accordingly, an object of the present invention is to provide an X-ray imaging apparatus, a medical image processing apparatus, an X-ray imaging method and a medical image processing method by which X-ray images useful for a diagnosis can be displayed as a 3D image for stereoscopic viewing with a simpler and more inexpensive structure.

DETAILED DESCRIPTION

In general, according to one embodiment, an X-ray imaging apparatus includes an X-ray image acquisition part, a control system and a display processing part. The X-ray image acquisition part is configured to acquire X-ray image data of an object using at least one imaging system. The control system is configured to control the imaging system to acquire frames of X-ray image data corresponding to mutually different directions by moving the imaging system. At least one of the frames of the X-ray image data are acquired during a movement of the imaging system. The display processing part is configured to generate stereoscopically visible image data based on the frames of the X-ray image data.

Further, according to another embodiment, a medical image processing apparatus includes an image acquisition part and a display processing part. The image acquisition part is configured to acquire frames of X-ray image data corresponding to not less than three different directions. The frames of the X-ray image data are acquired using a single imaging system. The display processing part is configured to generate stereoscopically visible image data based on the frames of the X-ray image data.

Further, according to another embodiment, an X-ray imaging method includes: acquiring X-ray image data of an object using at least one imaging system; controlling the imaging system to acquire frames of X-ray image data corresponding to mutually different directions by moving the imaging system; and generating stereoscopically visible image data based on the frames of the X-ray image data. At least one of the frames of the X-ray image data are acquired during a movement of the imaging system.

Further, according to another embodiment, a medical image processing method includes: acquiring frames of X-ray image data corresponding to not less than three different directions; and generating stereoscopically visible image data based on the frames of the X-ray image data. The frames of the X-ray image data are acquired using a single imaging system.

An X-ray imaging apparatus, a medical image processing apparatus, an X-ray imaging method and a medical image processing method according to embodiments of the present invention will be described with reference to the accompanying drawings.

Figure 1:
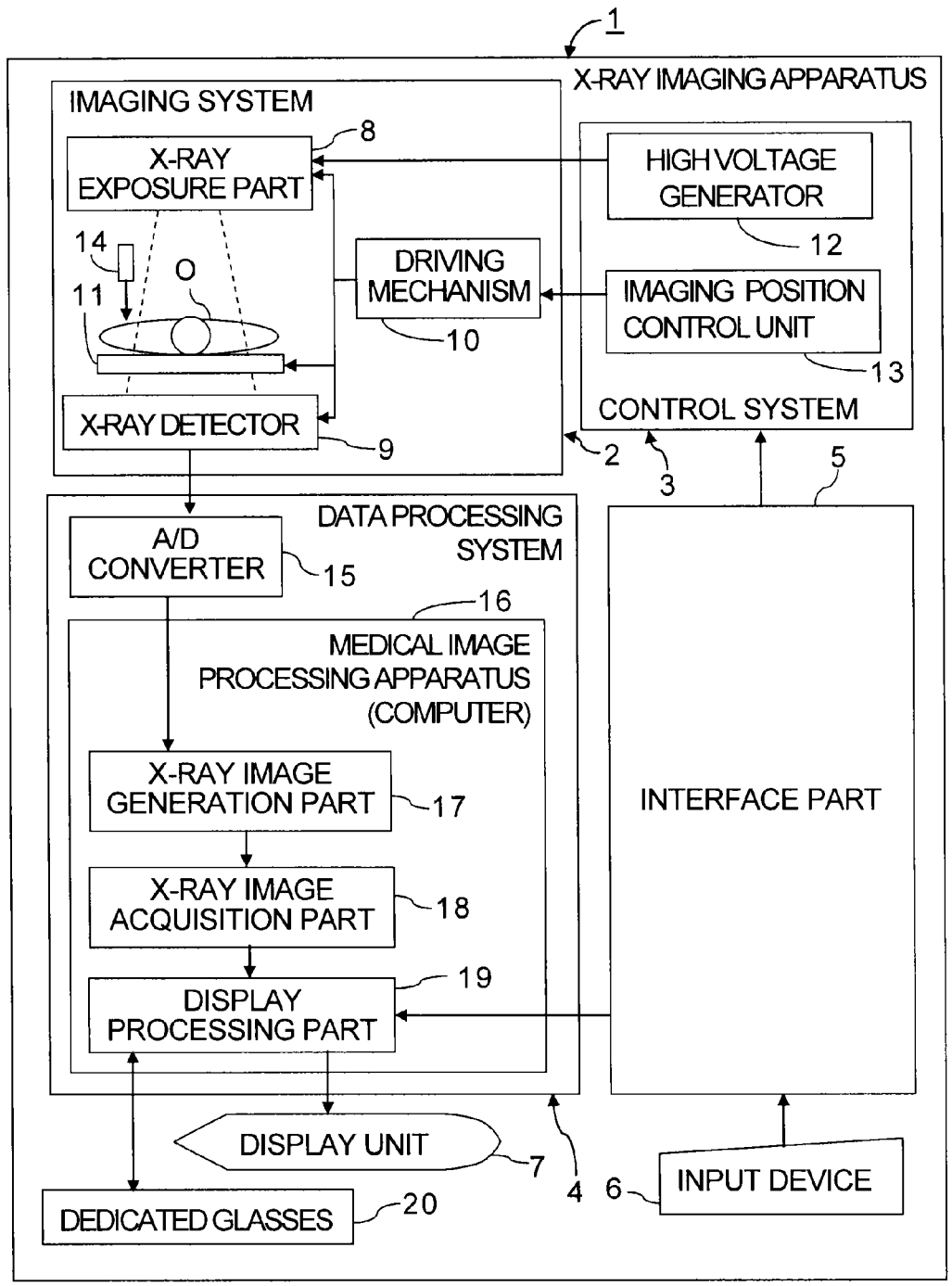
FIG. 1 is a configuration diagram of an X-ray imaging apparatus and a medical image processing apparatus according to one embodiment of the present invention.

FIG. 1 is a configuration diagram of an X-ray imaging apparatus and a medical image processing apparatus according to one embodiment of the present invention.

An X-ray imaging apparatus 1 includes an imaging system 2, a control system 3, and a data processing system 4, an interface part 5, an input device 6 and a display unit 7. The imaging system 2 has an X-ray exposure part 8, an X-ray detector 9, a driving mechanism 10 and a bed 11. The control system 3 has a high voltage generator 12 and an imaging position control unit 13.

The X-ray exposure part 8 includes an X-ray tube and is placed in the opposite side of the X-ray detector 9 so that an object O set on the bed 11 lies between the X-ray exposure part 8 and the X-ray detector 9. The X-ray exposure part 8 and the X-ray detector 9 can change the angle and the relative position with respect to the object O with keeping their relative position by driving the driving mechanism 10. Specifically, the X-ray exposure part 8 and the X-ray detector 9 are settled at both ends of the C-shaped arm having the rotational function. Then, the X-ray exposure part 8 is configured to expose an X-ray from a predetermined angle to an object O by the X-ray tube to detect the X-ray having transmitted the object O by the X-ray detector 9.

Moreover, the incline and the position of the table of the bed 11 can be adjusted with the driving mechanism 10. Therefore, the radiation direction of an X-ray toward an object O can be changed by adjusting not only the angle of the X-ray exposure part 8 and the X-ray detector 9 with regard to the object O but also the angle of the table.

Furthermore, a contrast medium injector 14 is provided in the vicinity of the object O set on the bed 11 in order to inject a contrast agent into the object O, as needed.

The high voltage generator 12 of the control system 3 is a unit which applies a high voltage to the X-ray tube of the X-ray exposure part 8 to expose an X-ray, having a desired energy, toward the object O. The imaging position control unit 13 is a unit which outputs a control signal to the driving mechanism 10 to control the driving mechanism 10. That is, the inclination and position of the top plate of the bed 11, and the rotation angle and position of the X-ray exposure part 8 and the X-ray detector 9 are controlled by the control signal output to the driving mechanism 10 from the imaging position control unit 13.

The data processing system 4 has an A/D (analog to digital) converter 15 and a computer 16. The computer 16 functions as a medical image processing apparatus 16 by executing programs. That is, the medical image processing apparatus 16 is built in the X-ray imaging apparatus 1.

However, an independent medical image processing apparatus having the similar function may be connected to the X-ray imaging apparatus 1 through a network. Moreover, circuits may be used for configuring the medical image processing apparatus 16 built in the X-ray imaging apparatus 1 or the medical image processing apparatus connected with the X-ray imaging apparatus 1 through a network. Meanwhile, the computer 16 may function as the interface part 5.

The medical image processing apparatus 16 has an X-ray image generation part 17, an X-ray image acquisition part 18 and a display processing part 19. The X-ray image generation part 17 has a function to read digitized X-ray detection data from the X-ray detector 9 through the A/D converter 15 to generate X-ray image data by data processing of the read X-ray detection data.

Therefore, the X-ray imaging apparatus 1 has a function as an X-ray image acquisition part, which acquires X-ray image data of an object O using the imaging system 2, by collaboration of the X-ray image generation part 17 with the imaging system 2 and the control system 3.

The X-ray image acquisition part 18 has a function to acquire the X-ray image data generated in the X-ray image generation part 17 and give the X-ray image data to the display processing part 19. Especially, in an independent medical image processing apparatus connected to the X-ray imaging apparatus 1 through a network, the X-ray image generation part 17 can be omitted. In this case, a function to acquire the X-ray image data from the X-ray image generation part 17 included in the X-ray imaging apparatus 1 through a network is provided with the X-ray image acquisition part 18.

The display processing part 19 has a function to acquire frames of X-ray image data including a frame of X-ray image data for left eye and a frame of X-ray image data for right eye from the X-ray image acquisition part 18; a function to generate 3D image data, as image data allowing stereoscopic viewing, based on the acquired frames of the X-ray image data; and a function to display the generated 3D image data on the display unit 7.

As a method of displaying a 3D image for stereoscopic viewing based on frames of X-ray image data for left eye and right eye, an arbitrary known method can be used. As typical methods, a method by using an usual display and a dedicated glasses and a method by using a dedicated display are known.

In case of using a dedicated glasses, a method of alternately indicating images for left eye and images for right eye with a constant temporal difference and preparing a function as a polarization plate with the dedicated glasses is known. In this case, circular polarized lights in mutually different rotational directions are given to the images for left eye and right eye. Thus, using a circular light glasses makes two-parallax images visible individually by the left and right eyes.

Alternatively, a method of indicating an image for left eye and an image for right eye as images in mutually different bands of wavelength with a time division is also known. In this case, the image for left eye and the image for right eye, which have transmitted a filter to become lights in the mutually different bands of wavelength, are visually recognized by the left and right eyes individually through a wavelength selection glasses.

Furthermore, another method for indicating images for left eye and images for right eye alternately with a time division so that the images for left eye and the images for right eye can be visually recognized with a glasses whose shutters for left eye and right eye open and close in synchronized with the time division is also known.

Conversely, a method for outputting positional information and directional information from a dedicated glasses and changing images to be output on a display according to the positional information and the directional information of the glasses is also known.

On the other hand, as a method without using a dedicated glasses, a method of overlapping a wave plate, having a phase difference, on the surface of a display, a method of overlapping a film, on which a convexoconcave having lines per inch different from a resolution of a display is arranged, on the surface of the display, and the like are known. Each of these methods is also called a spatial division method by which images for left eye and images for right eye are visually recognized by the left and right eyes respectively through a wave plate or a film.

Therefore, the X-ray imaging apparatus 1 has elements according to a displaying method of a 3D image. For example, a dedicated glasses 20 is connected with the computer 16 when it is required for the 3D display. Moreover, a dedicated display for 3D display is connected as the display unit 7 with the computer 16 when it is required for the 3D display. Thus, the display processing part 19 is configured to output and input information required for 3D display to one or both of the display unit 7 and the glasses 20.

On the other hand, the control system 3 has a function to control the single imaging system 2 in order to acquire frames of X-ray image data for left eye and right eye required for stereoscopic viewing. Specifically, the control system 3 has a function to control the imaging system 2 so that frames of X-ray image data corresponding to mutually different directions are acquired by moving the imaging system 2.

Especially, the control system 3 is configured to variably control a movement of the imaging system 2 and exposure timings or exposure positions of X-rays arbitrarily. For example, the imaging system 2 can be controlled so that frames of X-ray image data used as X-ray image data for left eye and X-ray image data for right eye are acquired in a static state of the imaging system 2. On the contrary, the imaging system 2 can be also controlled so that at least one of frames of X-ray image data used as X-ray image data for left eye and X-ray image data for right eye is acquired while the imaging system 2 is moving.

Then, the display processing part 19 is configured to generate X-ray image data for 3D display by display processing according to acquisition positions of frames of X-ray image data, having two or more parallaxes, acquired with moving the single imaging system 2. Specifically, using two frames of X-ray image data, corresponding to mutually different two directions, as two-parallax image data can generate one frame of image data which can be stereoscopically viewed from one direction. Alternatively, stereoscopic image data whose hue changes according to viewing directions, i.e., image data which can be stereoscopically viewed from mutually different directions can be generated based on frames of X-ray image data corresponding to three or more different directions.

Furthermore, the display processing part 19 is configured to generate stereoscopically visible image data with coordinate conversion processing of frames of X-ray image data so that the moving direction of the imaging system 2 becomes the horizontal direction on the display unit 7 for the stereoscopically visible image data, as needed. In addition, the display processing part 19 is configured to generate stereoscopically visible image data with a motion correction between frames of X-ray image data, corresponding to a same direction, acquired at mutually different timings by the imaging system 2, as needed.

Figure 2:
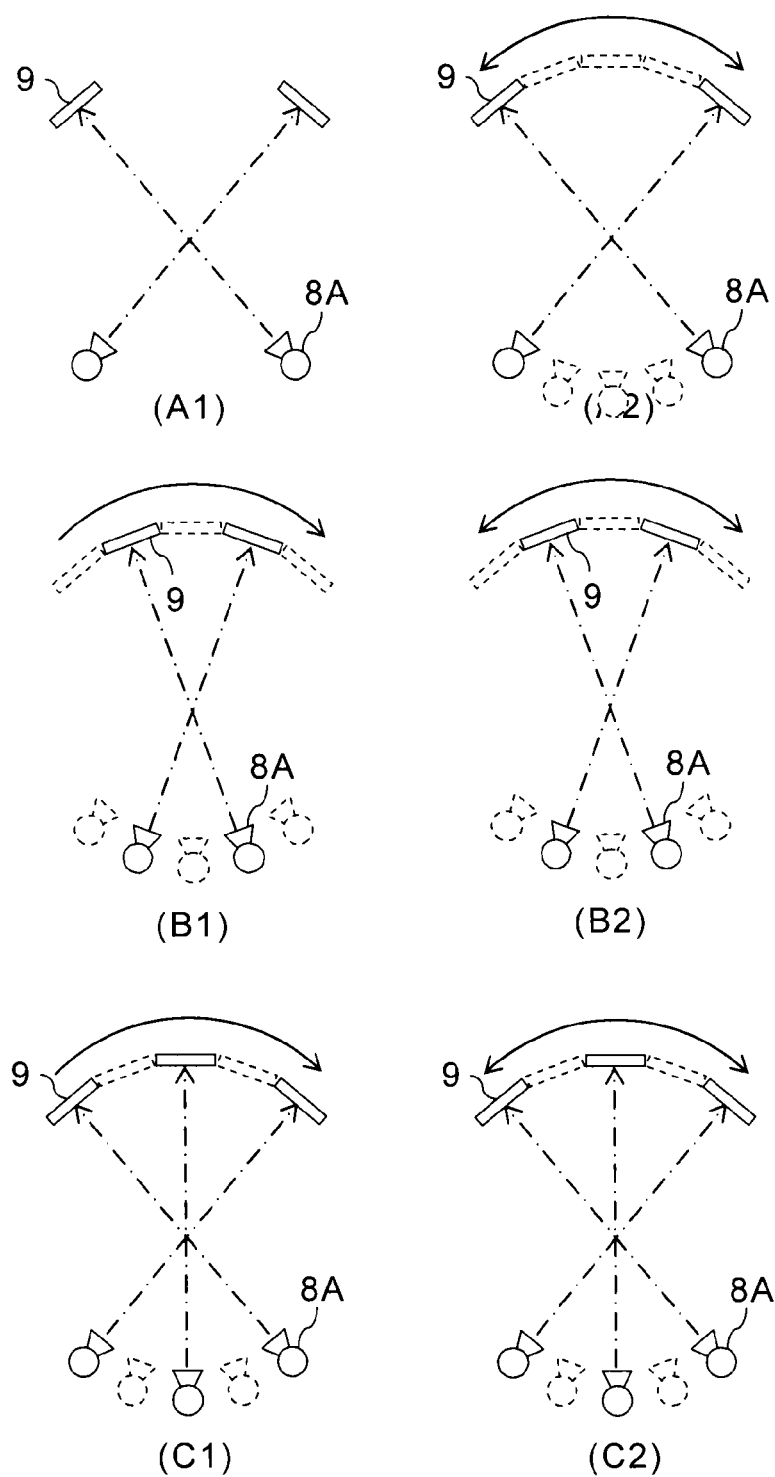
FIG. 2 shows examples of control method of the imaging system, for displaying X-ray images which can be stereoscopically viewed from one direction, in the X-ray imaging apparatus shown in FIG. 1.

FIG. 2 shows examples of control method of the imaging system, for displaying X-ray images which can be stereoscopically viewed from one direction, in the X-ray imaging apparatus 1 shown in FIG. 1.

As shown in FIG. 2 (A1), the X-ray tube 8A of the X-ray exposure part 8 and X-ray detector 9 can be stopped at two different positions sequentially by driving the driving mechanism 10 including the C-shaped arm to acquire two frames of X-ray image data corresponding to the respective positions of the X-ray tube 8A and the X-ray detector 9. Then, the two frames of the X-ray image data corresponding to the two different X-ray exposure directions can be used as one frame of X-ray image data having a two-parallax.

More specifically, the X-ray tube 8A and the X-ray detector 9 are positioned on the first position, and the X-ray image data for left eye corresponding to the first position is acquired in the condition that the X-ray tube 8A and the X-ray detector 9 are stopped. Next, the C-shaped arm is moved by a control of the control system 3, and the X-ray tube 8A and the X-ray detector 9 are positioned on the second position. Then, X-ray image data for right eye corresponding to the second position can be acquired in the condition that the X-ray tube 8A and the X-ray detector 9 are stopped. Alternatively, the X-ray image data for left eye may be acquired after acquiring the X-ray image data for right eye.

Moreover, by moving the C-shaped arm continuously, the imaging system 2 can be moved like a pendulum to acquire images repeatedly as shown in FIG. 2 (A2). That is, the imaging system 2 can be reciprocated to acquire X-ray image data sequentially at the both end positions.

Figure 3:
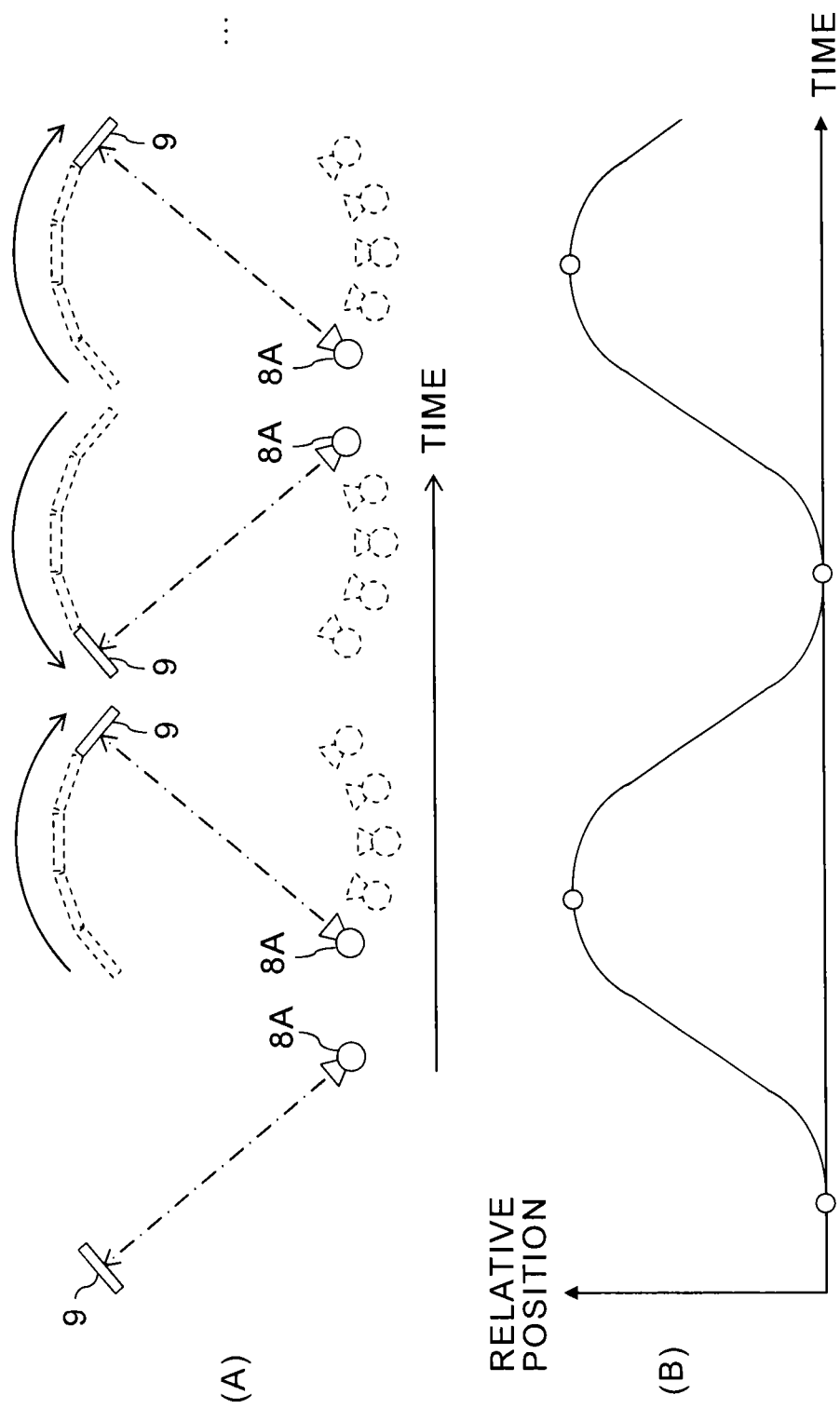
FIG. 3 shows the acquisition positions of X-ray image data in a time series in case of moving the X-ray tube and the X-ray detector as shown in FIG. 2 (A2)

FIG. 3 shows the acquisition positions of X-ray image data in a time series in case of moving the X-ray tube 8A and the X-ray detector 9 as shown in FIG. 2 (A2).

In FIG. 3 (A), the horizontal axis direction represents time. FIG. 3 (A) shows positions of the X-ray tube 8A and the X-ray detector 9 at acquisition timings of frames of X-ray image data. FIG. 3 (B) is a graph showing a time change in the relative position of the imaging system 2 including the X-ray tube 8A and the X-ray detector 9. That is, in FIG. 3 (B), the horizontal axis represents time while the vertical axis represents the relative position of the imaging system 2.

When the X-ray tube 8A and the X-ray detector 9 are reciprocated as shown in FIG. 2 (A2), X-ray image data for left eye and X-ray image data for right eye are sequentially and alternately acquired as shown in FIG. 3 (A). Therefore, the X-ray image data for left eye and the X-ray image data for right eye are alternately updated and indicated by the display processing part 19.

Note that, the velocity of the X-ray tube 8A and the X-ray detector 9 temporarily becomes zero at the turning points of the X-ray tube 8A and the X-ray detector 9. Therefore, as shown in FIG. 3 (B), the X-ray tube 8A and the X-ray detector 9 don't maintain a constant velocity, and the position of the X-ray tube 8A and the X-ray detector 9 changes periodically and nonlinearly like a pendulum motion. Then, as the marking points of FIG. 3 (B) show, the acquisition positions of the X-ray image data are at the local maximum and the local minimum.

The X-ray image data for left eye is constantly to be image data corresponding to a same X-ray exposure direction. Similarly, the X-ray image data for right eye is also constantly to be image data corresponding to another same X-ray exposure direction. Therefore, when the X-ray image data for left eye and the X-ray image data for right eye are sequentially updated and displayed as a 3D image, the 3D image is to be like a moving image from one observation direction.

However, a gantry having a C-shaped arm has a relatively large weight and a large force of inertia. For this reason, to acquire one frame of X-ray image data after acquiring another one frame of X-ray image data by moving a C-shaped arm, accelerations and stops of the heavy C-shaped arm are required. Therefore, an acquisition interval between two frames of X-ray image data becomes relatively long. As the result, influence of a motion of the object O may not be ignored between an acquisition timing of X-ray image data for left eye and an acquisition timing of X-ray image data for right eye.

Then, the imaging system 2 can be controlled so as to acquire frames of X-ray image data during a movement of the imaging system 2 including the X-ray tube 8A and the X-ray detector 9. Specifically, as shown in FIG. 2 (B1), the X-ray tube 8A and the X-ray detector 9 can be moved in one way to perform imaging twice within a moving period. In this case, two frames of X-ray image data corresponding to different positions, which are not on the both ends of the movement range of the imaging system 2, are inevitably acquired.

Then, the shorter the distance between acquisition positions of the two frames of the X-ray image data is, the shorter the acquisition intervals of the two frames of the X-ray image can be. For this reason, the influence of a motion of the object O can be reduced. Moreover, when the X-ray tube 8A and the X-ray detector 9 are at a position fully away from each of the both ends of the movement range, the moving speed of the X-ray tube 8A and the X-ray detector 9 is stable. For this reason, the X-ray image data itself can be stable.

Moreover, the shorter the moving distance of the X-ray tube 8A and the X-ray detector 9 is, the lower the exposure dose of the object O becomes. Therefore, it is suitable that the moving distance of the imaging system 2 is set to be the shortest distance required at least to have a stable moving speed of the X-ray tube 8A and the X-ray detector 9 at each imaging position.

In the case where frames of X-ray image data are acquired while the imaging system 2 is moving, the imaging system 2 can be also reciprocated like a pendulum by moving the C-shaped arm continuously. That is, as shown in FIG. 2 (B2), the imaging system 2 can be controlled so as to acquire frames of X-ray image data corresponding to mutually different directions in each of the outward way and the return way with reciprocating the imaging system 2.

Figure 4:
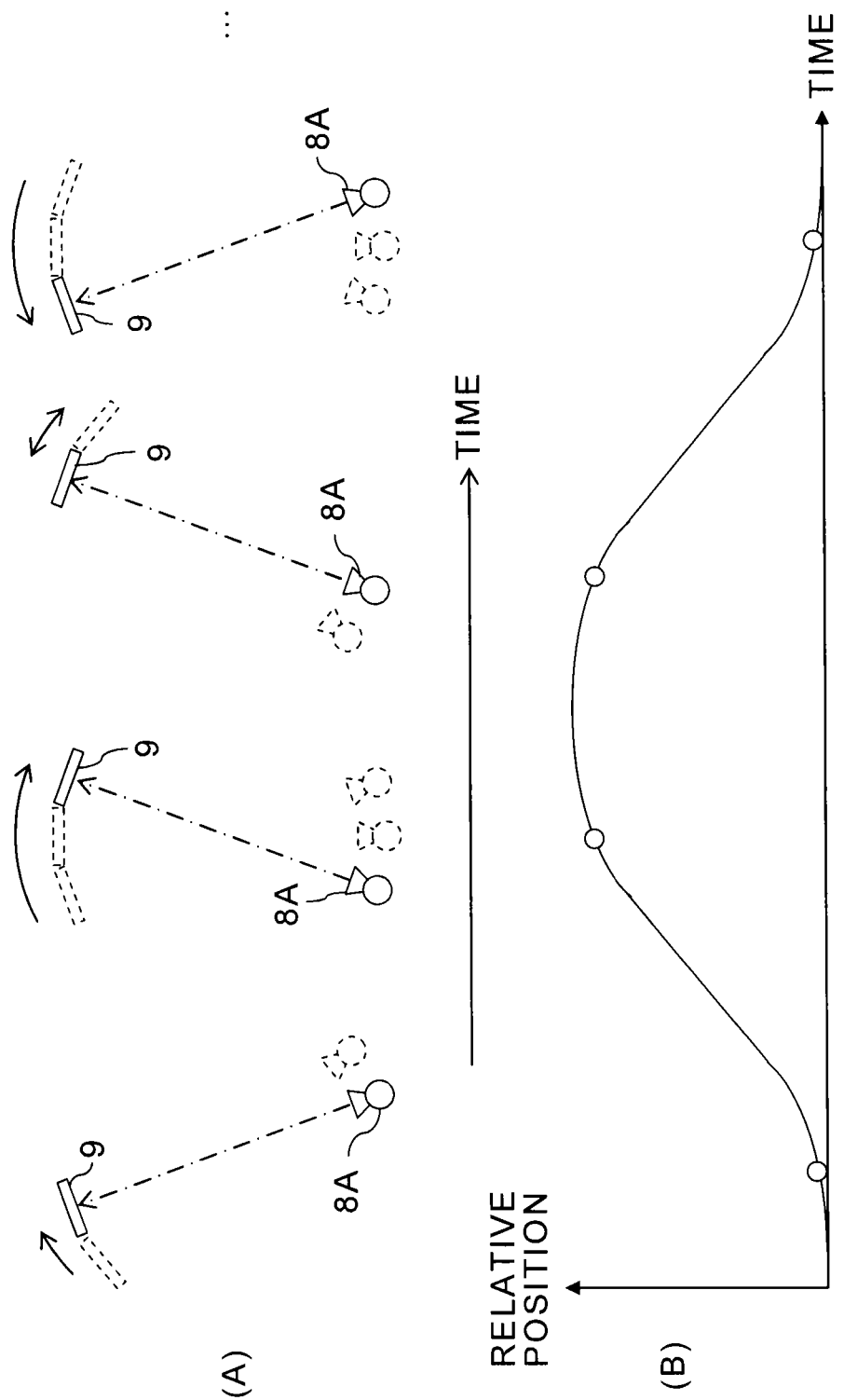
FIG. 4 shows the acquisition positions of X-ray image data in a time series in case of moving the X-ray tube and the X-ray detector as shown in FIG. 2 (B2)

FIG. 4 shows the acquisition positions of X-ray image data in a time series in case of moving the X-ray tube 8A and the X-ray detector 9 as shown in FIG. 2 (B2).

In FIG. 4 (A), the horizontal axis direction represents time. FIG. 4 (A) shows positions of the X-ray tube 8A and the X-ray detector 9 at acquisition timings of frames of X-ray image data. Moreover, FIG. 4 (B) is a graph showing a time change in the relative position of the imaging system 2 including the X-ray tube 8A and the X-ray detector 9. That is, in FIG. 4 (B), the horizontal axis represents time while the vertical axis represents the relative position of the imaging system 2.

When the X-ray tube 8A and the X-ray detector 9 are reciprocated to acquire two frames of X-ray image data while the X-ray tube 8A and the X-ray detector 9 are moving as shown in FIG. 2 (B2), X-ray image data for left eye and X-ray image data for right eye can be acquired at a short time interval as shown in FIG. 4 (A). Specifically, in the case shown in FIG. 3, three frames of X-ray image data are acquired during one reciprocation of the imaging system 2. On the contrary, in the case shown in FIG. 4, four frames of X-ray image data are acquired during one reciprocation of the imaging system 2. For this reason, an influence of a motion of the object O can be reduced.

Therefore, the scale of the time axis shown in FIG. 4 (B) differs from the scale of the time axis shown in FIG. 3 (B). Moreover, as the marking points of FIG. 4 (B) show, the acquisition positions of X-ray image data are two positions located between each local maximum and local minimum.

Moreover, not only the examples shown in FIG. 2 (B2) and FIG. 4, the imaging system 2 can be also controlled so as to acquire one frame of X-ray image data corresponding to a direction different between the outward way and the return way with reciprocating the imaging system 2.

Figure 5:
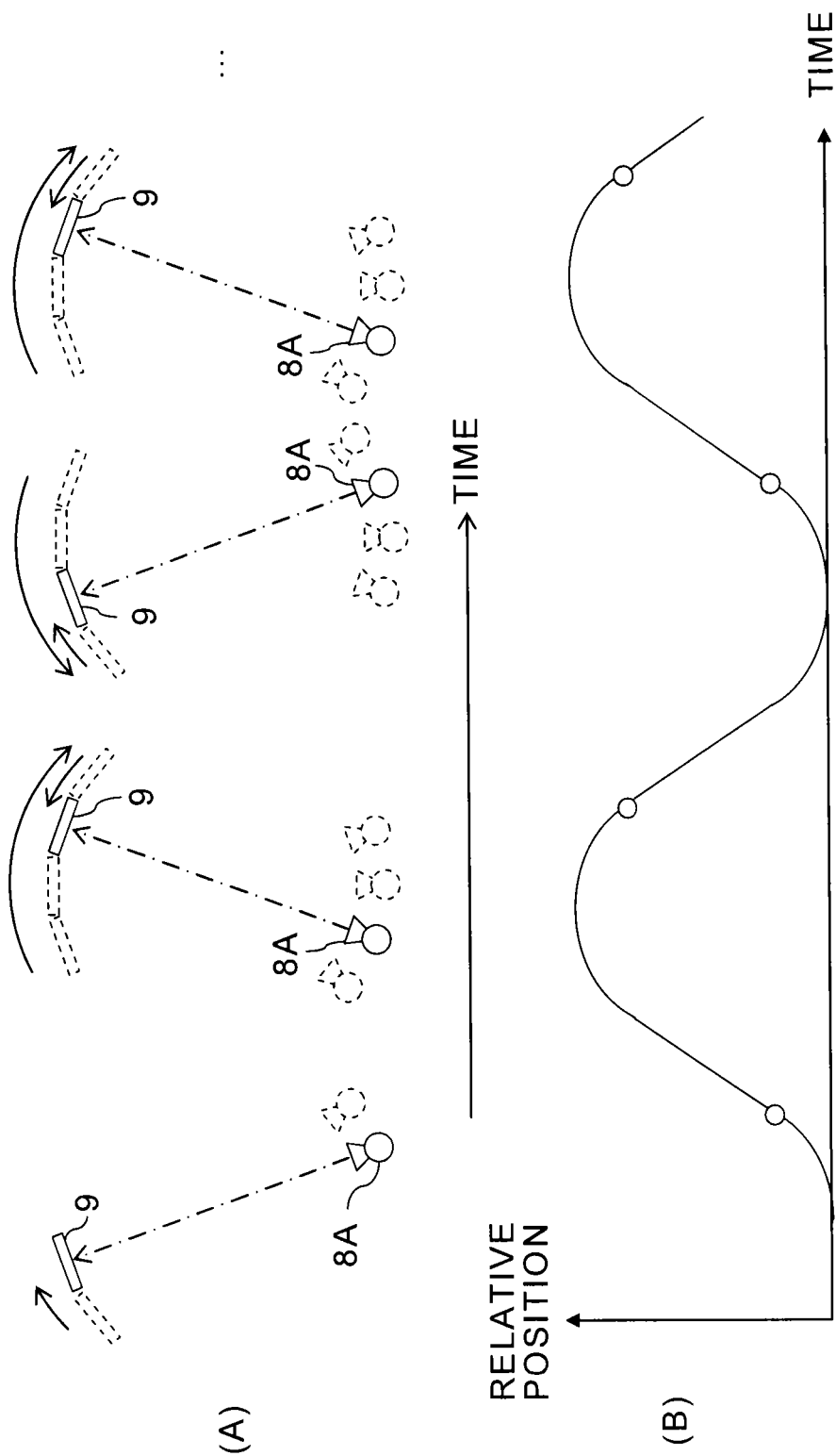
FIG. 5 shows the positions for acquiring frames of X-ray image data in a time series in case of acquiring X-ray image data for one frame in each of the accelerating periods in the outward way and the return way of the imaging system.

FIG. 5 shows the positions for acquiring frames of X-ray image data in a time series in case of acquiring X-ray image data for one frame in each of the accelerating periods in the outward way and the return way of the imaging system 2. Meanwhile, FIG. 6 shows the positions for acquiring frames of X-ray image data in a time series in case of acquiring X-ray image data for one frame in each of the decelerating periods in the outward way and the return way of the imaging system 2.

Figure 6:
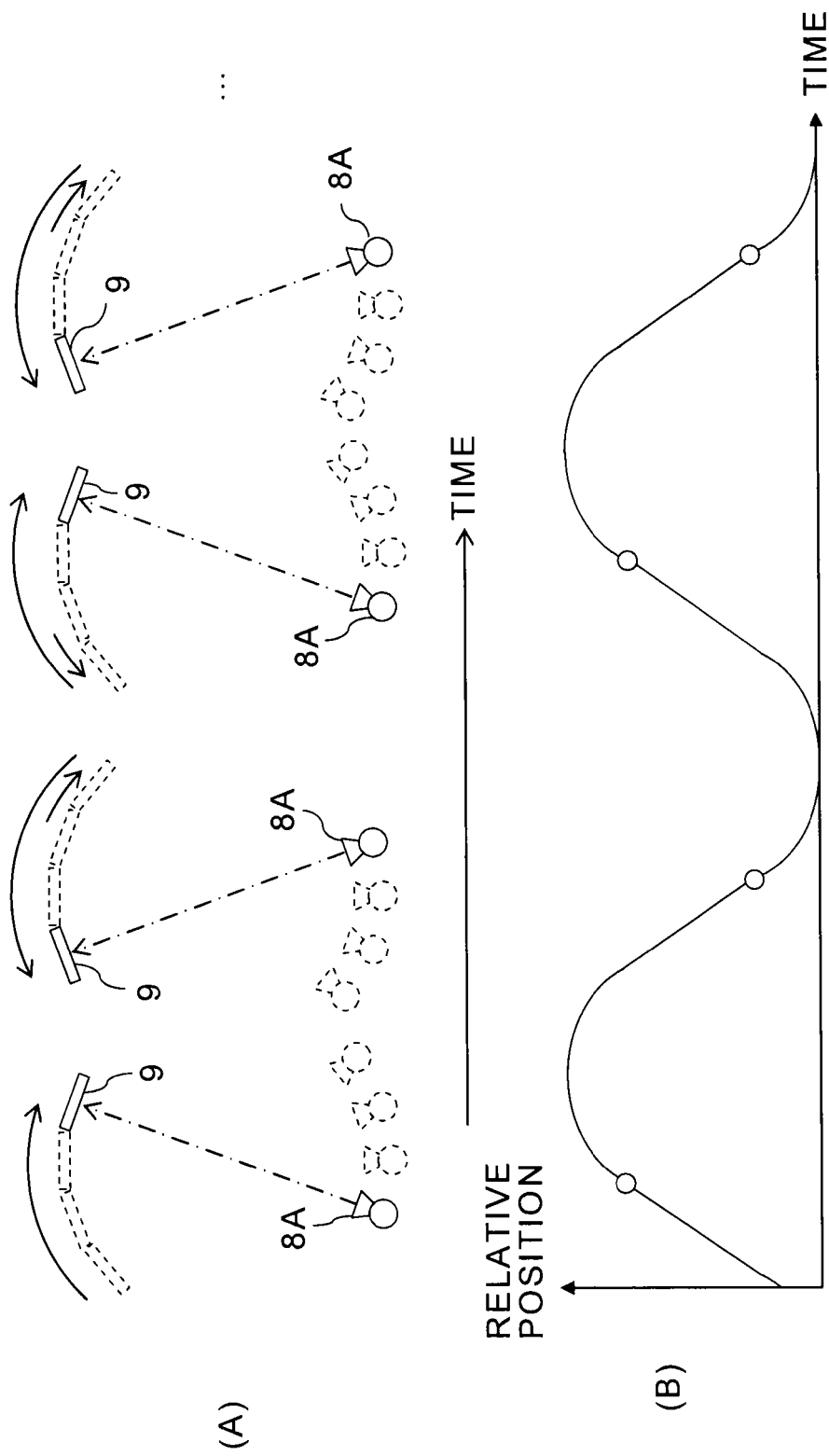
FIG. 6 shows the positions for acquiring frames of X-ray image data in a time series in case of acquiring X-ray image data for one frame in each of the decelerating periods in the outward way and the return way of the imaging system.

In FIG. 5 (A) and FIG. 6 (A), each horizontal axis direction represents time. FIG. 5 (A) and FIG. 6 (A) show positions of the X-ray tube 8A and the X-ray detector 9 at acquisition timings of frames of X-ray image data. Moreover, FIG. 5 (B) and FIG. 6 (B) are graphs each showing a time change in the relative position of the imaging system 2 including the X-ray tube 8A and the X-ray detector 9. That is, in each of FIG. 5 (B) and FIG. 6 (B), the horizontal axis represents time while the vertical axis represents the relative position of the imaging system 2.

As shown in FIG. 5, when X-ray image data is acquired while the X-ray tube 8A and the X-ray detector 9 move from one of the both ends of the movement range to the center position, the X-ray image data is to be acquired always in an accelerating period of the X-ray tube 8A and the X-ray detector 9. On the other hand, as shown in FIG. 6, when X-ray image data is acquired while the X-ray tube 8A and the X-ray detector 9 move from the center position of the movement range to one of the both ends, the X-ray image data is to be acquired always in an decelerating period of the X-ray tube 8A and the X-ray detector 9.

Therefore, when the imaging system 2 is controlled as shown in FIG. 5 or FIG. 6, X-ray image data can be acquired under a mechanically equivalent condition. That is, frames of image data for left eye and frames of image data for right eye can be acquired when the imaging system 2 is at the same movement velocity in each acquisition time. For this reason, display of stable 3D images is attained.

Besides the above examples, X-ray image data other than X-ray image data for left eye and X-ray image data for right eye can be also acquired at an arbitrary position as shown in FIG. 2 (C1). Then, the X-ray image data acquired at an arbitrary position can be used for display processing for a 3D display. In the example shown in FIG. 2 (C1), the X-ray image data corresponding to the center position of the movement range of the imaging system 2 is acquired. However, X-ray image data for a 3D display may be acquired aside from the acquisition of the X-ray image data for left eye and the X-ray image data for right eye.

X-ray image data except for X-ray image data for left eye and X-ray image data for right eye can be used for arbitrary processing according to diagnostic purposes, such as compound processing with X-ray image data for left eye and X-ray image data for right eye. Moreover, X-ray image data other than X-ray image data for left eye and X-ray image data for right eye can be also acquired continuously and repeatedly with a reciprocation of the imaging system 2 as shown in FIG. 2 (C2).

Some examples of control method of the imaging system 2 for displaying X-ray images for which stereoscopic viewing is allowed from one direction have been explained up to here. Furthermore, the imaging system 2 can be also controlled so as to display X-ray images for which stereoscopic viewing is allowed from plural directions. In order to display X-ray images for which stereoscopic viewing is allowed from plural directions, two or more different sets of two-parallax image data are required. Therefore, it is necessary to acquire some frames of X-ray image data corresponding to three or more different X-ray exposure directions.

These explained below are highly practical examples for controlling the imaging system 2 to acquire frames of X-ray image data corresponding to not less than three different directions while the imaging system 2 is moving in at least one direction or is in static condition.

Figure 7:
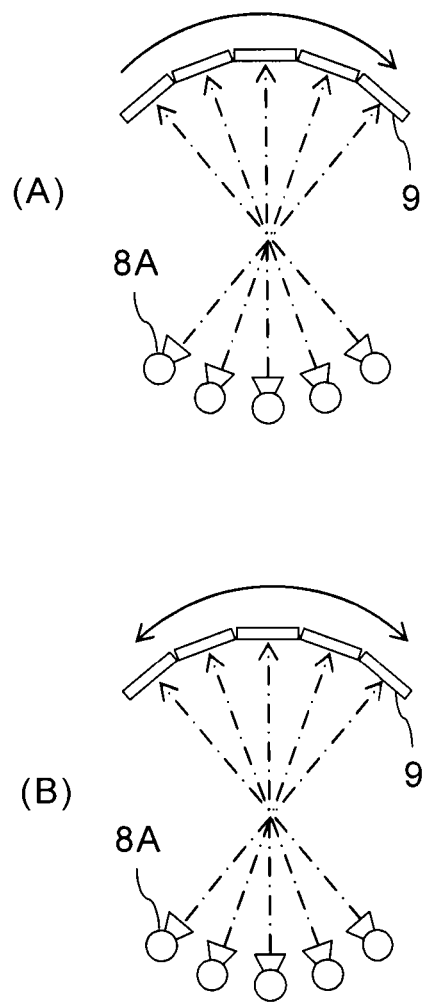
FIG. 7 shows examples of control method of the imaging system, for displaying X-ray images which can be stereoscopically viewed from plural directions, in the X-ray imaging apparatus shown in FIG. 1.

FIG. 7 shows examples of control method of the imaging system 2, for displaying X-ray images which can be stereoscopically viewed from plural directions, in the X-ray imaging apparatus 1 shown in FIG. 1.

As shown in FIG. 7 (A), the single imaging system 2 can be moved in one direction so that frames of X-ray image data corresponding to not less than three different directions are acquired during a movement or a static condition. On the other hand, as shown in FIG. 7 (B), the single imaging system 2 may be reciprocated like a pendulum so that frames of X-ray image data corresponding to not less than three different directions are acquired in each of the outward way and the return way. In this case, at least one of the frames of the X-ray image data used as X-ray image data for left eye and X-ray image data for right eye is to be acquired during the movement of the imaging system 2.

When the imaging system 2 is controlled by the control system 3 as shown in FIG. 7, frames of X-ray image data, corresponding to not less than three different directions, acquired using the single imaging system 2 are acquired in the image acquisition part 18. For this reason, the display processing part 19 can generate 3D image data allowing stereoscopic viewing by various ways, based on the frames of the X-ray image data corresponding to the different directions.

Figure 8:
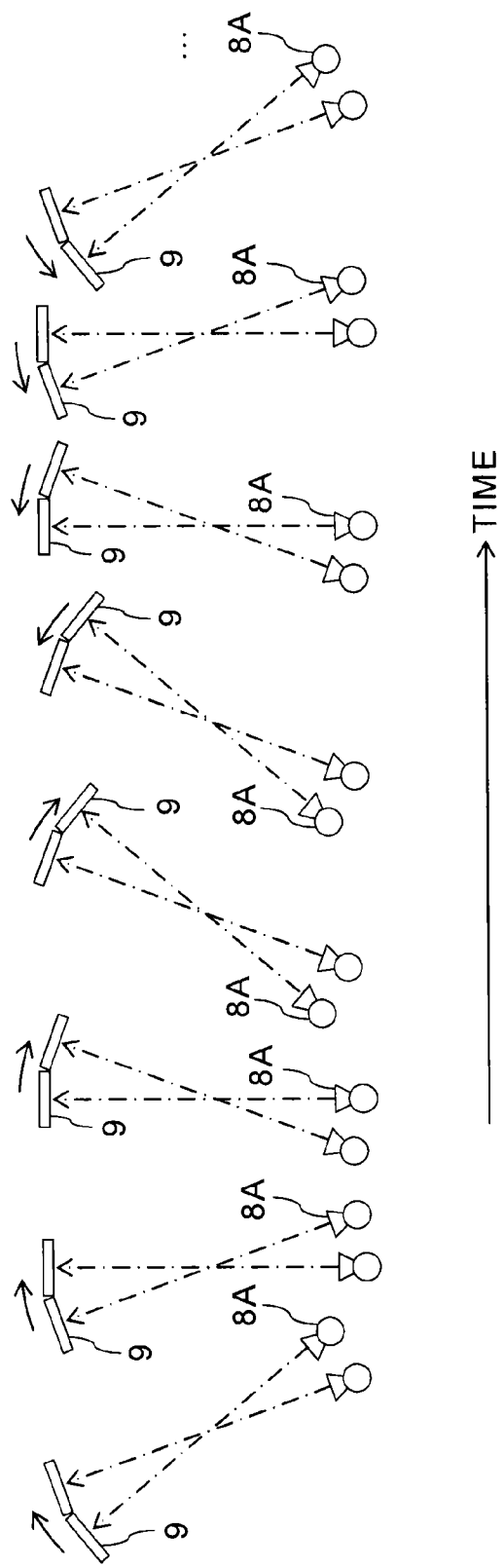
FIG. 8 is a view showing the first example of display processing in the display processing part for displaying X-ray images which can be stereoscopically viewed from plural directions.

FIG. 8 is a view showing the first example of display processing in the display processing part 19 for displaying X-ray images which can be stereoscopically viewed from plural directions.

In FIG. 8, the horizontal axis direction represents time. Moreover, the respective positions of the X-ray tube 8A and the X-ray detector 9 shown in FIG. 8 represent acquisition positions of frames of X-ray image data displayed as one frame of stereoscopic image.

As shown in FIG. 8, frames of image data, which can be stereoscopically viewed from mutually different directions, can be generated by sequentially generating one frame of image data, allowing stereoscopic viewing, based on two frames of X-ray image data corresponding to two different directions. That is, the imaging system 2 can be reciprocated continuously and a newly acquired image and an image acquired in the past can be indicated and updated as a pair of two-parallax images.

When the display control of stereoscopic images as shown in FIG. 8 is performed, one of images which constitute a stereoscopic image is updated and the pair of two-parallax images changes whenever a new image is acquired. Therefore, the stereoscopic images serve as a moving image to which the viewpoint changes sequentially. Accordingly, an imaged target is to be seen with a rotation.

Note that, images which are not adjacent may be used as a pair of two-parallax images although the adjacent images are used as a pair of two-parallax images in the examples shown in FIG. 8. It is experientially suitable for effective stereoscopic viewing that the difference in angle between exposure directions of X-rays exposed in order to acquire two images used as a pair of two-parallax images is set within the range from 1 degree to 3 degrees. Therefore, it is most effective to set the angle difference, between X-ray exposure directions corresponding to a pair of two-parallax images, to 2 degrees. This is the same also in a display of a pair of two-parallax images mentioned later.

Figure 9:
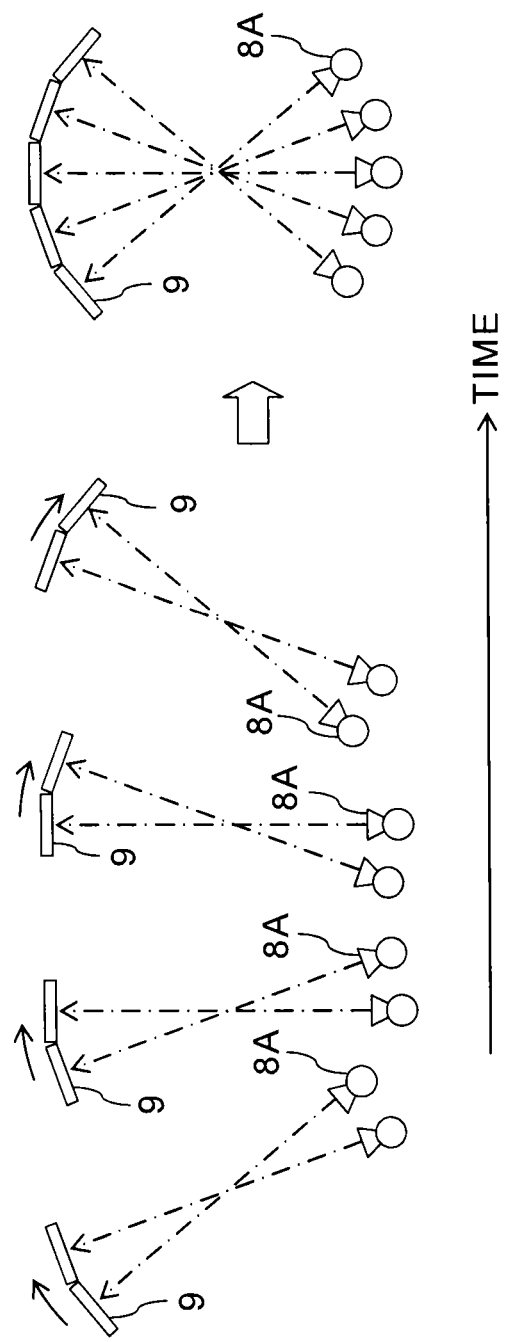
FIG. 9 is a view showing the second example of display processing in the display processing part for displaying X-ray images which can be stereoscopically viewed from plural directions.

FIG. 9 is a view showing the second example of display processing in the display processing part 19 for displaying X-ray images which can be stereoscopically viewed from plural directions.

In FIG. 9, the horizontal axis direction represents time. Moreover, the respective positions of the X-ray tube 8A and the X-ray detector 9 shown in FIG. 9 represent acquisition positions of frames of X-ray image data displayed as one frame of stereoscopic image.

As shown in FIG. 9, frames of image data, which can be stereoscopically viewed from mutually different directions, can be generated by sequentially generating one frame of image data, allowing stereoscopic viewing, based on two frames of X-ray image data corresponding to two different directions. That is, the imaging system 2 is moved in one direction and a newly acquired image and an image acquired in the past can be subsequently indicated and updated as a pair of two-parallax images. Therefore, the stereoscopic images can be displayed as a moving image of which the viewpoint of two-parallax images changes sequentially, similarly to the example shown in FIG. 8.

After that, as shown in FIG. 9, one frame of image data which can be stereoscopically viewed from mutually different directions can be generated based on frames of X-ray image data corresponding to not less than three different directions. That is, not less than three images, corresponding to mutually different directions, acquired in the past can be displayed as one frame of multi-parallax image.

Therefore, when the display control as shown in FIG. 9 is performed, a multi-parallax image is displayed as a still image after displaying a moving image of two-parallax images whose imaging target is viewed with a rotation.

Note that, multi-parallax images are a stereoscopic image whose hue changes depending on a viewing angle. Specifically, a display control of multi-parallax images is performed by the display processing part 19 according to a display method of stereoscopic images. For example, when the dedicated glasses 20 are used, a detection result of an angle sensor or a position sensor equipped with the glasses 20 is output to the display processing part 19. Then, the display processing part 19 detects a viewing angle of stereoscopic image and eye-positions of a user based on information acquired from the glasses 20. Moreover, the display processing part 19 can perform a switching control of images to be displayed, according to the viewing angle of the stereoscopic image and the eye-positions of the user.

On the other hand, when a dedicated display unit is used for displaying stereoscopic images, pixels of X-ray images corresponding to not less than three different directions are displayed in a range of one period of a phase plate or a convexoconcave pitch on a film having a convexoconcave. As a result, a stereoscopic image whose hue changes according to a viewing direction can be displayed.

Figure 10:
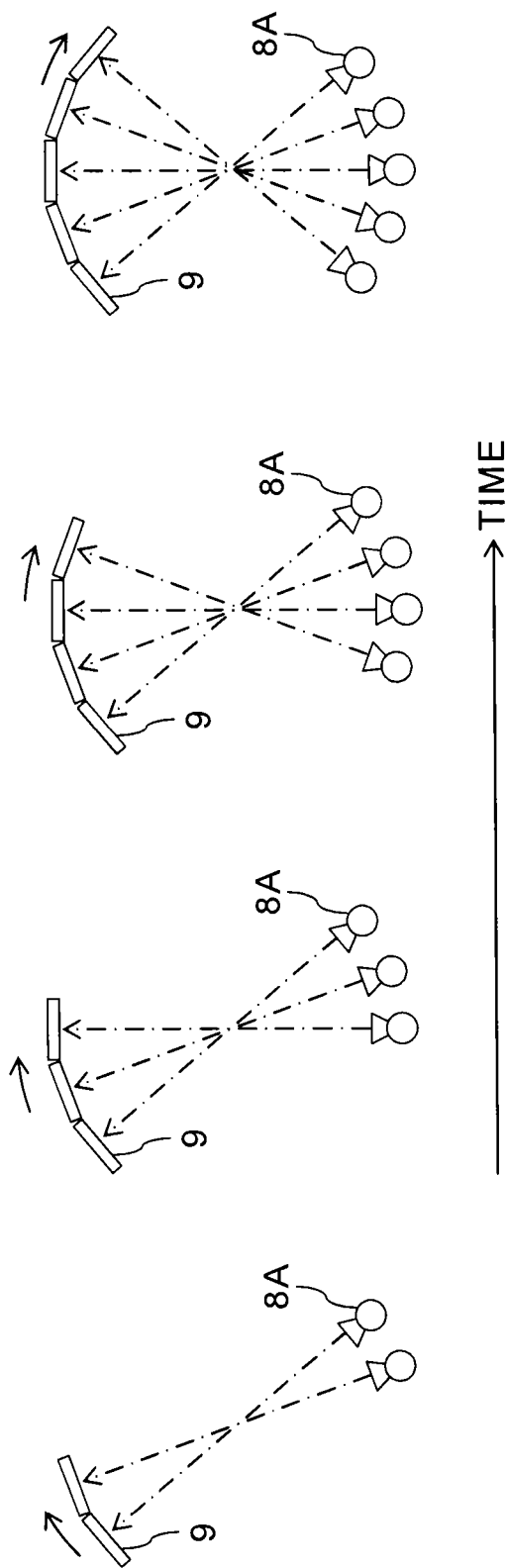
FIG. 10 is a view showing the third example of display processing in the display processing part for displaying X-ray images which can be stereoscopically viewed from plural directions.

FIG. 10 is a view showing the third example of display processing in the display processing part 19 for displaying X-ray images which can be stereoscopically viewed from plural directions.

In FIG. 10, the horizontal axis direction represents time. Moreover, the respective positions of the X-ray tube 8A and the X-ray detector 9 shown in FIG. 10 represent acquisition positions of frames of X-ray image data displayed as one frame of stereoscopic image.

As shown in FIG. 10, the imaging system 2 is moved in one direction. Then, a newly acquired image can be added sequentially to be displayed as multi-parallax images. In this case, viewing directions from which hues are different from each other increase whenever an image is acquired. Moreover, images acquired in the past are still displayed even after an image is newly acquired. Therefore, the imaging target is viewed as a still image without a motion.

Figure 11:
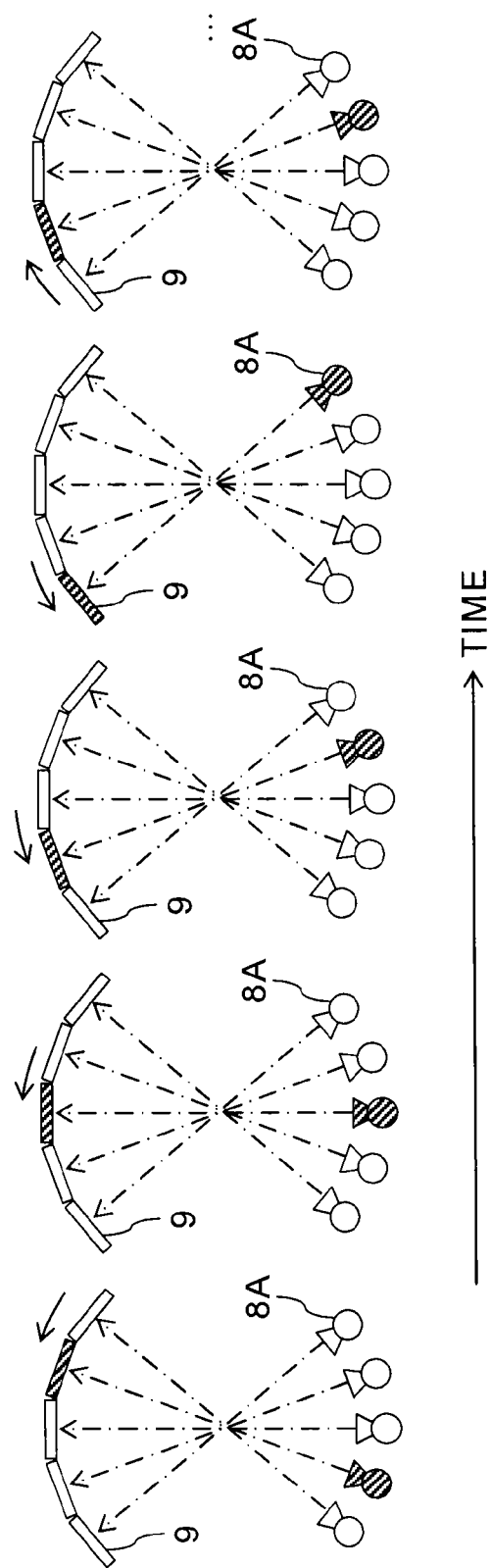
FIG. 11 is a view showing an example of display control for multi-parallax images by the display processing part shown in FIG. 1.

FIG. 11 is a view showing an example of display control for multi-parallax images by the display processing part 19 shown in FIG. 1.

In FIG. 11, the horizontal axis direction represents time. After displaying multi-parallax images acquired by moving the imaging system 2 in one direction as shown in FIG. 9 or FIG. 10, images can be acquired by continuously moving the imaging system 2 in the opposite direction. That is, images for multi-parallax images can be acquired repeatedly by reciprocating the imaging system 2.

In this case, multi-parallax images can be updated by replacing an image acquired in the past with an image newly acquired at the corresponding position. As a result, multi-parallax images acquired at timings closer to an observation time can be displayed for stereoscopic viewing. Note that, the positions of the X-ray tube 8A and the X-ray detector 9 shown with hatched lines in FIG. 11 represent the positions of images to be replaced.

Furthermore, as mentioned above, when a direction of images which are sequentially updated and added with a movement of the imaging system 2 is not the right and left direction of a user, a coordinate conversion can be performed by the display processing part 19. That is, coordinate conversion of each frame of image data to be a display target can be performed so that the direction of the images which are sequentially updated and added with a movement of the imaging system 2 becomes the right and left direction of the display unit 7 and the user.

Thereby, stereoscopic images which allow stereoscopic viewing with the right and left eyes, whichever direction the imaging system 2 moves in, can be displayed. Moreover, by changing a pair of two-parallax images in time or displaying multi-parallax images, a stereoscopic image whose hue changes in the right and left direction can be displayed. For example, a stereoscopic image can be displayed appropriately even in a case where the imaging system 2 is moved in the CRA (cranial) direction and the CAU (caudal) direction as well as a case where the imaging system 2 is moved in the LAO (left anterior oblique) direction and the RAO (right anterior oblique) direction.

Figure 12:
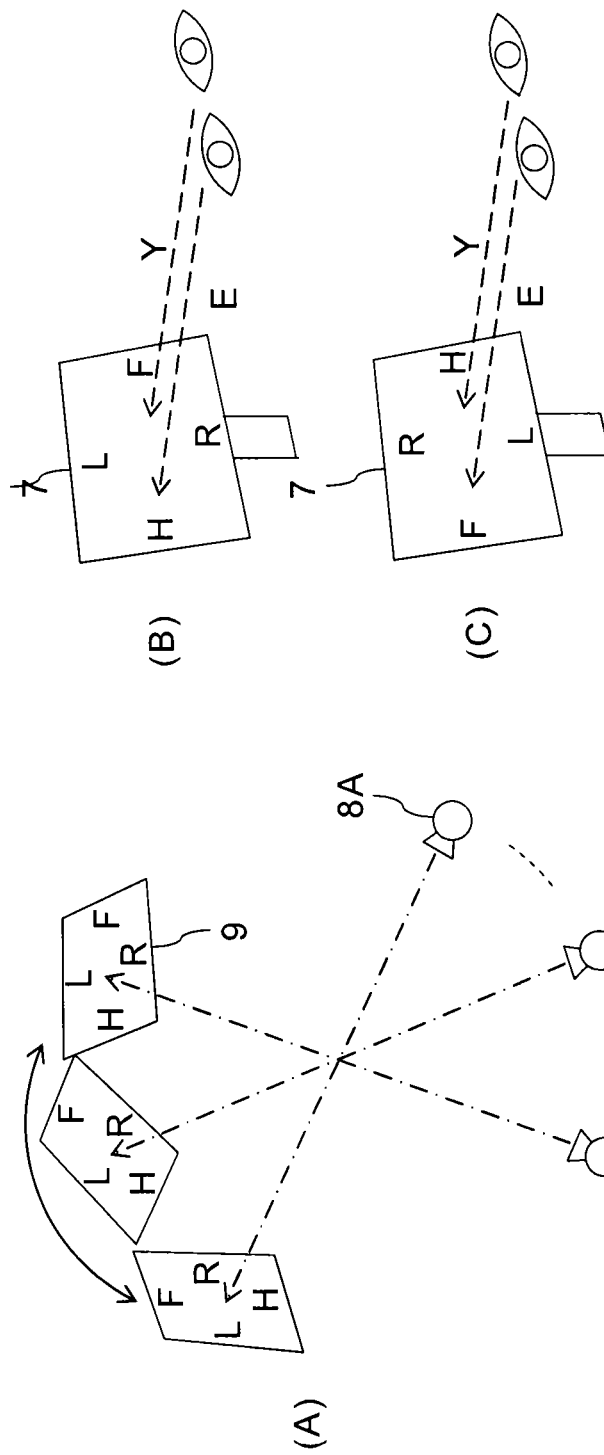
FIG. 12 is a view showing an example of coordinate conversion possibly performed by the display processing part shown in FIG. 1.

FIG. 12 is a view showing an example of coordinate conversion possibly performed by the display processing part 19 shown in FIG. 1.

Even in a case where the X-ray tube 8A and the X-ray detector 9 are swung in the HF (Head Foot) direction of the object O to acquire images sequentially as shown in FIG. 12 (A), the images can be displayed so that the HF direction becomes the horizontal direction of the display unit 7 as shown in FIG. 12 (B) and FIG. 12 (C). That is, a swing direction of the imaging system 2 can become the horizontal direction of the display unit 7 by coordinate conversion processing, such as rotation processing or inversion processing, of X-ray image data. Thereby, the HF direction which is the swing direction of the imaging system 2 becomes the direction between eye directions Y and E by the right and left eyes.

As a result, an image for right eye and an image for left eye, whose positions are mutually shifted in the horizontal direction according to the eye directions Y and E by the right and left eyes, can be displayed on the display unit 7. Then, display of a stereoscopic image to allow a stereoscopic sense by the right and left eyes having a parallax becomes possible.

Furthermore, as mentioned above, motion correction processing can be performed by the display processing part 19 prior to displaying images for a stereoscopic viewing. In a case where images are acquired by a reciprocation of the imaging system 2, the images are acquired discretely in time as shown in (B) of each of FIG. 3 to FIG. 6. Some mechanical positional gaps may result slightly in images due to a movement of the imaging system 2 on acquiring the images even in the condition that the X-ray tube 8A and the X-ray detector 9 are controlled so as to move to a same position. If the mages for a stereoscopic viewing have positional gaps, the gaps may cause that the images are seen swinging. In addition, a motion of the object O may occur.

Accordingly, a motion correction can be performed between frames of image data acquired under a control for moving the X-ray tube 8A and the X-ray detector 9 on a same position. As the motion correction, arbitrary known processing can be used. Examples of the motion correction include one for correcting a positional gap between two frames of image data to be corrected and one for correcting a positional gap between a frame of image data to be corrected and reference image data.

As for the motion correction itself, a linear correction and a nonlinear correction of pixel values of image data are known. The linear correction includes parallel translation, rotational transfer and expansion and contraction transformation of pixel values. Meanwhile, the nonlinear correction also includes parallel translation, rotational transfer and expansion and contraction transformation of pixel values by using an arbitrary function. The image data after the motion correction can be acquired as a result of an optimization calculation for moving pixel values so as to maximize a cross-correlation function between two frames of image data or an optimization calculation for minimizing an index value of discrepancy amount, such as least square errors or sum of total pixel values of subtraction image data.

Note that, a device or a marker attached with a device depicted in image data can be used as a landmark for the motion correction. In this case, processing, such as edge detection processing or threshold processing, for detecting a landmark is performed as a part of the motion correction. Consequently, a position-gap correction to move pixel values of image data linearly or nonlinearly can be performed based on a motion distance of an extracted landmark.

The control methods of the imaging system 2, the display methods of a stereoscopic image, necessity of the coordinate conversion, and necessity of the motion correction as mentioned above can be set up through the interface part 5 shown in FIG. 1. The control methods of the imaging system 2 include whether the imaging system 2 is reciprocated, X-ray exposure directions to acquire frames of X-ray image data, and so on, as options. The X-ray exposure directions to acquire frames of X-ray image data can be directly or indirectly set. For example, the X-ray exposure directions can be indirectly set as positions of the imaging system 2, a pitch of rotation angle of the imaging system 2, or an interval of exposure timing of X-rays. On the other hand, the display methods of a stereoscopic image include whether two-parallax images are displayed as a moving image or multi-parallax images are displayed, in case of acquiring X-ray images corresponding to not less than three different directions, and the like, as options.

Accordingly, a control method of the imaging system 2 and a display method of a stereoscopic image can be selected from plural imaging modes and plural display modes respectively. That is, a setting screen of the control methods of the imaging system 2 and the like can be displayed on the display unit 7. Then, the imaging modes and the display modes can be displayed as selectable modes on the display unit 7. Moreover, for setting the necessity of the coordinate conversion and the necessity of the motion correction, switching buttons between on/off may be displayed on the setting screen, for example.

Thus, a user can input information for specifying control methods of the imaging system 2, display methods of stereoscopic images, necessity of coordinate conversion, and necessity of motion correction, into the interface part 5 with operation of the input device 6. On the other hand, the interface part 5 is configured to output control information of the imaging system 2 to the control system 3 and to output display conditions of stereoscopic images to the display processing part 19, according to the input specification information.

That is, the interface part 5 functions as a specification part configured to specify at least one of necessity of reciprocation of the imaging system 2, different directions to acquire frames of X-ray image data, and frames of X-ray image data used for generating one frame of stereoscopically visible image data.

Next, an operation and an action of the X-ray imaging apparatus 1 will be explained.

First, the interface part 5 displays a setting screen of imaging conditions, including control methods of the imaging system 2 and display methods of stereoscopic images, on the display unit 7. On this setting screen, various operation modes of the imaging system 2 and various display modes of stereoscopic images as shown in FIG. 2 to FIG. 11 can be selected. Therefore, a user can select an appropriate operation mode of the imaging system 2 and an appropriate display mode of stereoscopic images by operating the input device 6 in consideration of conditions such as an image quality required for a diagnosis and exposure doses of the object O.

In addition, executions of coordinate conversion processing and motion correction processing can be set as display processing conditions, as needed. Besides, a user sets other imaging conditions necessary for acquiring stereoscopic images of an imaging part of the object O or the like through the setting screen of imaging conditions.

On the other hand, an object O is set on the top plate of the bed 11. Moreover, a contrast agent is injected into the object O from the contrast medium injector 14, if needed. Then, the start of an imaging is directed to the interface part 5 with an operation of the input device 6. Thereby, the interface part 5 outputs the control information of the imaging system 2 to the control system 3 according to a selected operation mode of the imaging system 2. On the other hand, the interface part 5 notifies a display method of stereoscopic image to the display processing part 19, according to a selected display mode of stereoscopic image.

Then, control signals corresponding to the operation mode of the imaging system 2 are output from the imaging position control unit 13 of the control system 3 to drive the driving mechanism 7. Thereby, the X-ray exposure part 8 and the X-ray detector 9 move according to the operation mode.

On the other hand, a high voltage is applied to the X-ray tube 8A of the X-ray exposure part 8 from the high voltage generator 12 of the control system 3 according to the operation mode. Thereby, an X-ray is exposed to an imaging part of the object O from the X-ray tube 8A at timing at which the X-ray tube 8A and the X-ray detector 9 are on the predetermined position with the predetermined rotational angle. Then, the X-ray which transmitted the object O is detected by the X-ray detector 9.

Next, an X-ray detection signal is output to the medical image processing apparatus 16 from the X-ray detector 9 through the A/D converter 15. Thereby, the digitized X-ray detection data is acquired in the X-ray image generation part 17. Then, the X-ray image generation part 17 generates X-ray image data by known data processing of the X-ray detection data.

The X-ray image data generated in the X-ray image generation part 17 is given to the X-ray image acquisition part 18. Then, frames of X-ray image data corresponding to at least two X-ray exposure directions are acquired sequentially in the X-ray image acquisition part 18 in the same flow. Especially, in a case of generating two-parallax images or multi-parallax images corresponding to plural observation directions, frames of X-ray image data corresponding to at least three X-ray exposure directions are acquired, and are obtained in the X-ray image acquisition part 18.

Next, the X-ray image acquisition part 18 gives the frames of the X-ray image data to the display processing part 19. Then, the display processing part 19 displays X-ray images, which can stereoscopically viewed, on the display unit 7 according to a display format of stereoscopic image and the display method of stereoscopic image acquired from the interface part 5. For example, in case of displaying an image for left eye and an image for right eye with a time division, X-ray image data acquired for left eye and X-ray image data acquired for right eye are subjected to the time division in the display processing part 19 to be output to the display unit 7.

Note that, when one or both of the coordinate conversion and the motion correction of X-ray image data have been directed through the interface part 5, one or both of the coordinate conversion and the motion correction are performed in the display processing part 19. Consequently, X-ray image data having image qualities suitable for a stereoscopic viewing can be acquired from appropriate directions.

Thereby, a user can stereoscopically view X-ray images displayed on the display unit 7 through the dedicated glasses 20. For example, when a pair of two-parallax images are repeatedly acquired at the same positions, stereoscopic images can be observed as a moving image. Alternatively, in the case where a pair of two-parallax images are repeatedly acquired and the acquisition positions of the pair of the two-parallax images change, stereoscopic images can be observed as a moving image whose observation direction changes with time. Furthermore, when images having not less than three parallaxes are displayed, a stereoscopic image whose hue changes according to a viewing direction can be observed.

That is, the above mentioned X-ray imaging apparatus 1 is configured to acquire frames of X-ray image data by moving the single imaging system 2 under various control methods to display a stereoscopic image in various display methods by using the acquired frames of the X-ray image data.

Accordingly, by using the X-ray imaging apparatus 1, stereoscopic images can be displayed with image qualities and hues suitable for a diagnostic purpose. That is, the imaging system 2 can be controlled by different operating methods according to purposes, such as observing a structure of a blood vessel and checking a direction of a wire. Then, stereoscopic images can be displayed using X-ray images for stereoscopic viewing acquired by the control of the imaging system 2, in various display methods according to moving methods of the imaging system 2 and purposes.

Especially, even for a same imaging target, display methods of stereoscopic images can be changed according to diagnostic purposes. For example, in case of stereoscopic viewing of an organ or the like, the purpose may be a diagnosis, an observation of an anatomical structure for a treatment planning, confirmation of a direction of the present operated device during a treatment or the like. For this reason, stereoscopic images can be generated and displayed with selecting imaging methods and display methods suitable for a purpose. As a specific example, a user can select imaging methods for stereoscopic images and display methods corresponding to the imaging methods with consideration of various conditions, such as image qualities required for stereoscopic images, exposure doses of the object O, and an injected quantity of a contrast agent.

Moreover, according to the X-ray imaging apparatus 1, stereoscopic images can be generated and displayed by using the single imaging system 2. In addition, the X-ray imaging apparatus 1 does not need complicate three dimensional image reconstruction processing for generating and displaying stereoscopic images. Therefore, stereoscopic images can be generated and displayed by a very cheap and simple composition and data processing. In other words, even the X-ray imaging apparatus 1 having the single imaging system 2 can generate and display stereoscopic images which are not inferior to those which can be generated in an X-ray imaging apparatus having plural imaging systems or an X-ray imaging apparatus performing advanced three dimensional image reconstruction processing.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, although a case where two-parallax images for a 3D image allowing stereoscopic viewing are acquired by using the X-ray imaging apparatus having the single imaging system has been explained in the above-mentioned example, similar two-parallax images can be also acquired in an X-ray imaging apparatus having plural imaging systems by using one of the plural imaging systems. That is, two-parallax images for a 3D image can be acquired by using an X-ray imaging apparatus which acquires X-ray image data of an object using at least one imaging system.

Figure 13A:
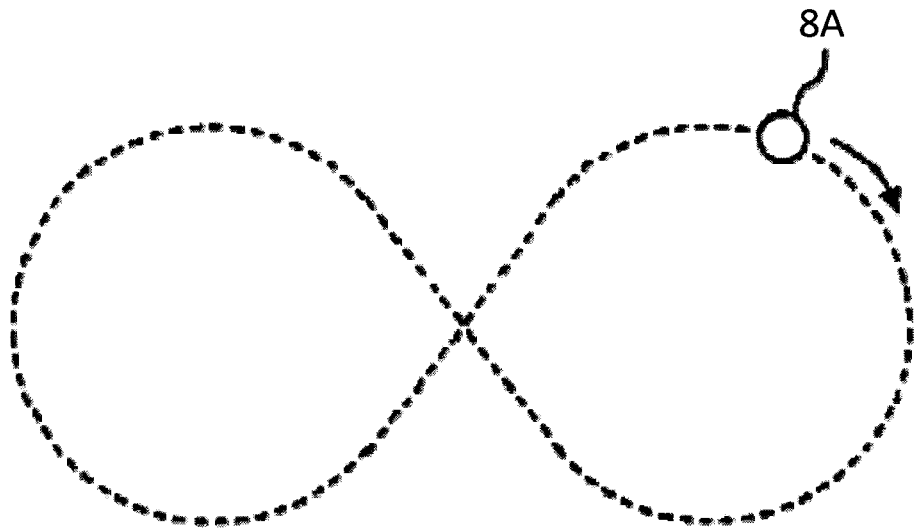
FIG. 13A shows an example of a locus having a projection on a plane in a shape of a character of eight.
Figure 13B:
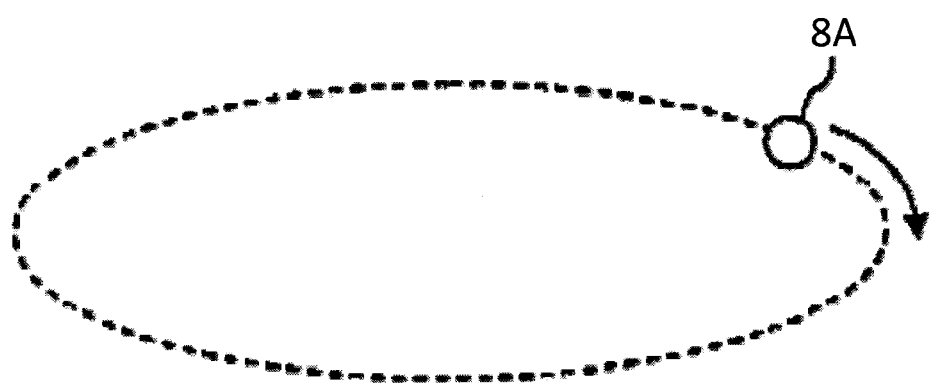
FIG. 13B shows an example of a locus having a projection on a plane in a shape of an ellipse.

Furthermore, although the above-mentioned example explains the case where the control system 3 moves the imaging system 2 along with a locus of a pendulum on a plane, it is also possible to move the imaging system 2 so that a locus of the imaging system 2 becomes one of a pendulum when the locus of the imaging system 2 is projected on a plane. As a specific example, the imaging system 2 can be moved along with a locus having a shape of an ellipse or a character of eight, as shown in FIG. 13B and FIG. 13A respectively. In this case, a high-speed imaging is attained since the imaging system 2 does not stand still.

What is claimed is:
1. An X-ray imaging apparatus comprising:
   at least one imaging system, having an X-ray tube and an X-ray detector, configured to acquire X-ray image data of an object;
   a control system configured to control the imaging system to acquire frames of the X-ray image data corresponding to mutually different directions by moving the imaging system, the frames of the X-ray image data being acquired during a movement of the imaging system; and a display processing circuit configured to generate stereoscopically visible image data based on the frames of the X-ray image data, acquired during movement of the imaging system and corresponding to positions which are between and not including ends of a movement range of the imaging system.

2. An X-ray imaging apparatus of claim 1,
wherein said control system is configured to control the imaging system to reciprocate the imaging system to acquire the frames of the X-ray image data corresponding to mutually different directions in each of an outward way and a return way of the imaging system.

3. An X-ray imaging apparatus of claim 1,
wherein said control system is configured to control the imaging system to acquire the frames of the X-ray image data corresponding to not less than three different directions while the imaging system is moving in at least one direction; and
said display processing circuit is configured to generate the frames of image data, which can be stereoscopically viewed from mutually different directions, by sequentially generating one frame of stereoscopically visible image data based on two frames of the X-ray image data corresponding to two different directions.

4. An X-ray imaging apparatus of claim 1,
wherein said control system is configured to control the imaging system to acquire the frames of the X-ray image data corresponding to not less than three different directions while the imaging system is moving in at least one direction; and
said display processing circuit is configured to generate one frame of image data, which can be stereoscopically viewed from mutually different directions, based on the frames of the X-ray image data corresponding to the not less than three different directions.

5. An X-ray imaging apparatus of claim 1,
wherein said display processing circuit is configured to generate the stereoscopically visible image data with coordinate conversion processing of the frames of the X-ray image data, the coordinate conversion processing converting a direction of the frames of the X-ray image data, corresponding to a moving direction of the imaging system, to a horizontal direction of a display unit for the stereoscopically visible image data.

6. An X-ray imaging apparatus of claim 1, further comprising:
a specification circuit configured to specify at least one of whether the imaging system is reciprocated, the different directions to acquire the frames of the X-ray image data, and the frames of the X-ray image data used for generating one frame of the stereoscopically visible image data.

7. An X-ray imaging apparatus of claim 1,
wherein said display processing circuit is configured to generate the stereoscopically visible image data with a motion correction between the frames of the X-ray image data, corresponding to a same direction, acquired at mutually different timings by the imaging system.

8. An X-ray imaging apparatus of claim 1,
wherein said control system is configured to move the imaging system along a locus having a shape of an ellipse or a character of eight, a projection of the locus on a plane being pendular.

9. An X-ray imaging apparatus of claim 1,
wherein said display processing circuit is configured to generate the stereoscopically visible image data based on the frames of the X-ray image data acquired during an accelerating period or on decelerating period of the imaging system.

10. An X-ray imaging apparatus of claim 1,
wherein a difference in angle between exposure directions of X-rays exposed in order to acquire two-parallax images consisting of the stereoscopically visible image data is set within a range from 1 degree to 3 degrees.

11. A medical image processing apparatus comprising:
an image acquisition circuit configured to acquire frames of X-ray image data corresponding to not less than three different directions, the frames of the X-ray image data being acquired using a single imaging system, the frames of the X-ray image data being acquired during a movement of the imaging system and corresponding to positions which are between and not including ends of a movement range of the imaging system; and
a display processing circuit configured to generate stereoscopically visible image data based on the frames of the X-ray image data.

12. A medical image processing apparatus of claim 11,
wherein said display processing circuit is configured to generate frames of image data, which can be stereoscopically viewed from mutually different directions, by sequentially generating one frame of stereoscopically visible image data based on two frames of the X-ray image data corresponding to two different directions.

13. A medical image processing apparatus of claim 11,
wherein said display processing circuit is configured to generate one frame of image data, which can be stereoscopically viewed from mutually different directions, based on the frames of the X-ray image data corresponding to the not less than three different directions.

14. An X-ray imaging method comprising:
acquiring X-ray image data of an object using at least one imaging system;
controlling the at least one imaging system to acquire frames of the X-ray image data corresponding to mutually different directions by moving the at least one imaging system, the frames of the X-ray image data being acquired during a movement of the at least one imaging system; and
generating stereoscopically visible image data based on the frames of the X-ray image data, acquired during the movement of the at least one imaging system and corresponding to positions which are between and not including ends of a movement range of the imaging system.

15. A medical image processing method comprising:
acquiring frames of X-ray image data corresponding to not less than three different directions, the frames of the X-ray image data being acquired using a single imaging system, the frames of the X-ray image data being acquired during a movement of the imaging system and corresponding to positions which are between and not including ends of a movement range of the imaging system; and
generating stereoscopically visible image data based on the frames of the X-ray image data.

* * * * *